US008622908B2

(12) United States Patent
Matsumura

(10) Patent No.: US 8,622,908 B2
(45) Date of Patent: Jan. 7, 2014

(54) PRESSING MEMBER, ULTRASONIC PROBE AND ULTRASONIC DIAGNOSING DEVICE

(75) Inventor: Takeshi Matsumura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1344 days.

(21) Appl. No.: 11/814,692

(22) PCT Filed: Jan. 26, 2006

(86) PCT No.: PCT/JP2006/301229
§ 371 (c)(1),
(2), (4) Date: Dec. 2, 2008

(87) PCT Pub. No.: WO2006/080399
PCT Pub. Date: Aug. 3, 2006

(65) Prior Publication Data
US 2009/0177083 A1 Jul. 9, 2009

(30) Foreign Application Priority Data

Jan. 26, 2005 (JP) .................................. 2005-017803

(51) Int. Cl.
*A61B 8/00* (2006.01)
(52) U.S. Cl.
USPC ........... 600/437; 600/439; 600/443; 600/447; 600/449; 600/458; 600/459
(58) Field of Classification Search
USPC .......................... 600/437, 439, 447, 449, 459
See application file for complete search history.

(56) References Cited

U.S. PATENT DOCUMENTS

| 4,688,578 | A | * | 8/1987 | Takano et al. ................. 600/459 |
| 5,203,333 | A | * | 4/1993 | Nomura ........................ 600/439 |
| 5,394,877 | A | | 3/1995 | Orr et al. |
| 5,524,636 | A | * | 6/1996 | Sarvazyan et al. ............ 600/587 |
| 5,947,904 | A | * | 9/1999 | Hossack et al. ............... 600/458 |
| 7,901,357 | B2 | * | 3/2011 | Boctor et al. ................. 600/443 |
| 7,914,456 | B2 | * | 3/2011 | Osaka et al. .................. 600/447 |
| 2002/0104385 | A1 | * | 8/2002 | Imai et al. .................. 73/861.27 |
| 2003/0212422 | A1 | * | 11/2003 | Fenton et al. ................. 606/169 |
| 2005/0059891 | A1 | * | 3/2005 | Kosaku ........................ 600/439 |
| 2005/0085728 | A1 | * | 4/2005 | Fukuda ........................ 600/449 |

FOREIGN PATENT DOCUMENTS

| JP | 58-85090 | 5/1983 |
| JP | 59-190209 | 10/1984 |
| JP | 2004-147984 | 5/2004 |
| JP | 2005-013283 | 1/2005 |
| JP | 2005-066041 | 3/2005 |
| JP | 2007-105400 | 4/2007 |
| WO | WO 2004/105615 | 12/2004 |

* cited by examiner

*Primary Examiner* — Baisakhi Roy
(74) *Attorney, Agent, or Firm* — Antonelli, Terry, Stout & Kraus, LLP.

(57) ABSTRACT

An object is to provide a pressing member, an ultrasonic probe and an ultrasonic diagnosing device that enhance the efficiency of uniformly pressing a subject and achieve a high-precision elastic image. Therefore, the contact surface of the pressing member with the subject is formed so that the vertical direction of the face of at least a part of the contact surface is different from the vertical direction of the face of the other part. The pressing member is detachably mounted on the probe or formed integrally with the probe.

12 Claims, 14 Drawing Sheets

FIG. 1B
(a)
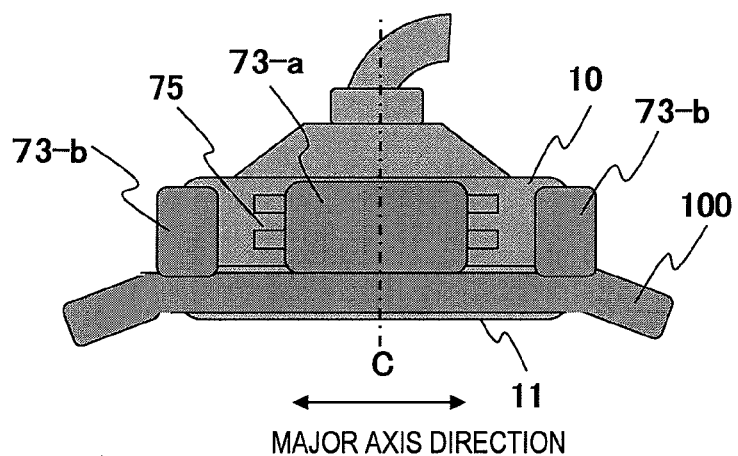
MAJOR AXIS DIRECTION
(b)
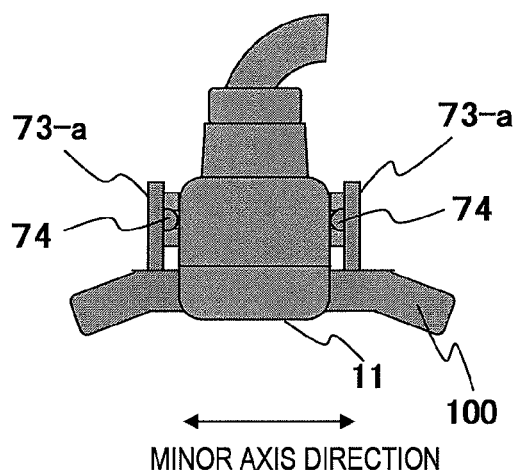
MINOR AXIS DIRECTION
(c)
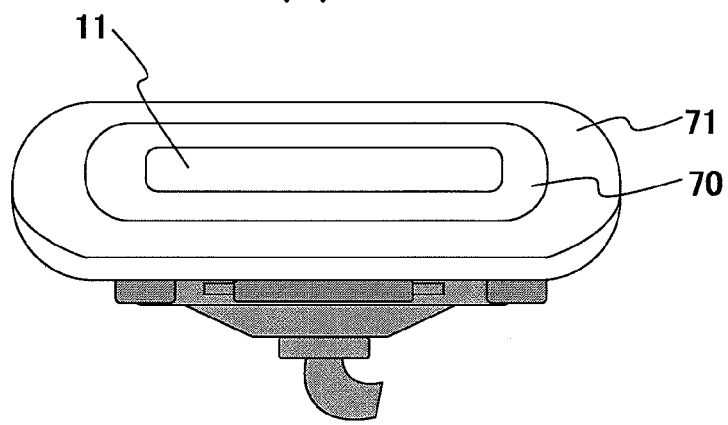

FIG. 1C
(a)
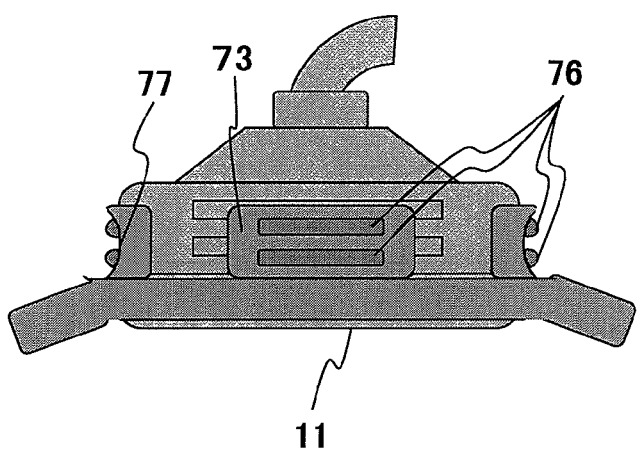
(b)
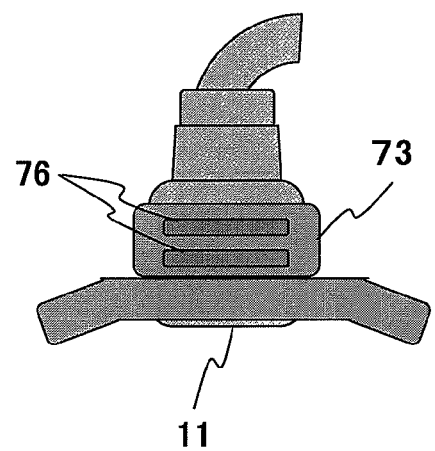
(c)
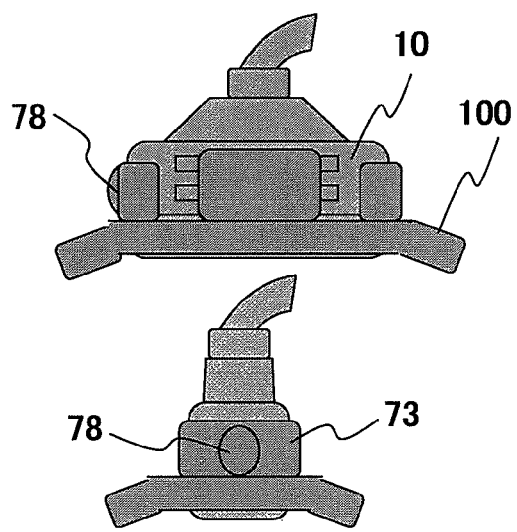
(d)
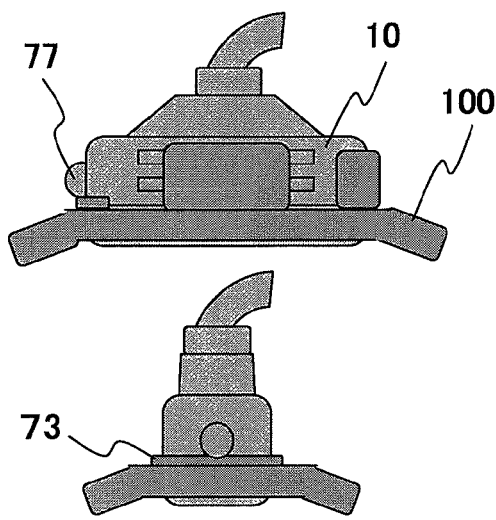

FIG. 1D
(a)
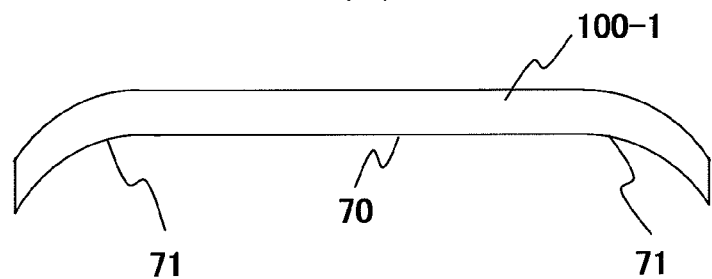
(b)
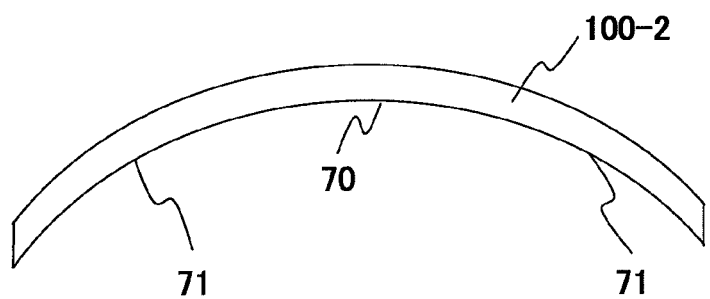
(c)
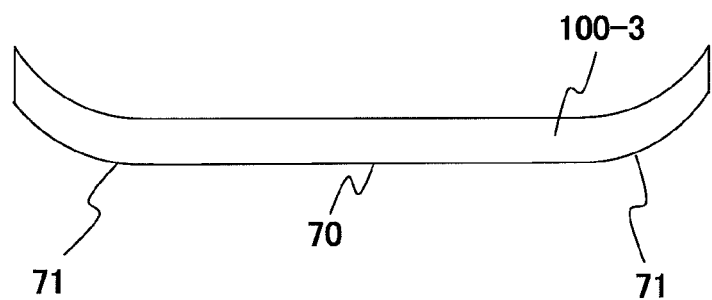
(d)
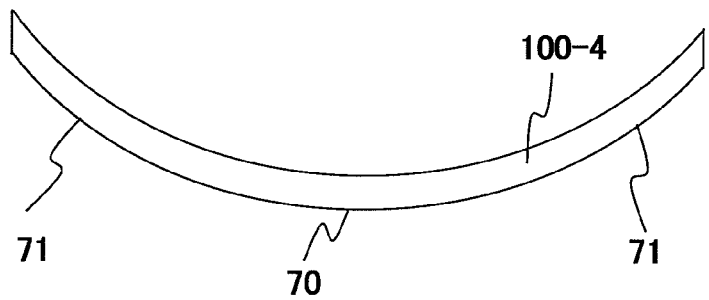

FIG. 4
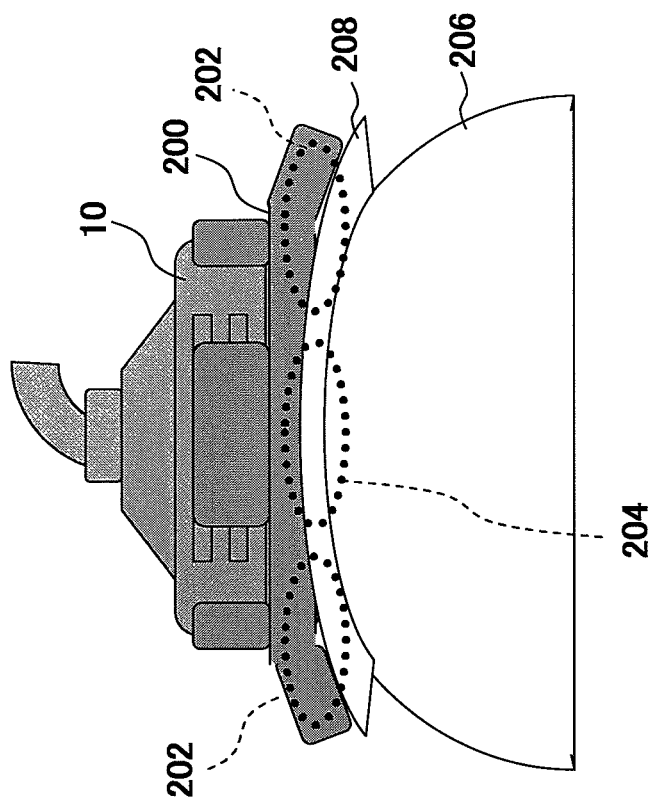
(a)
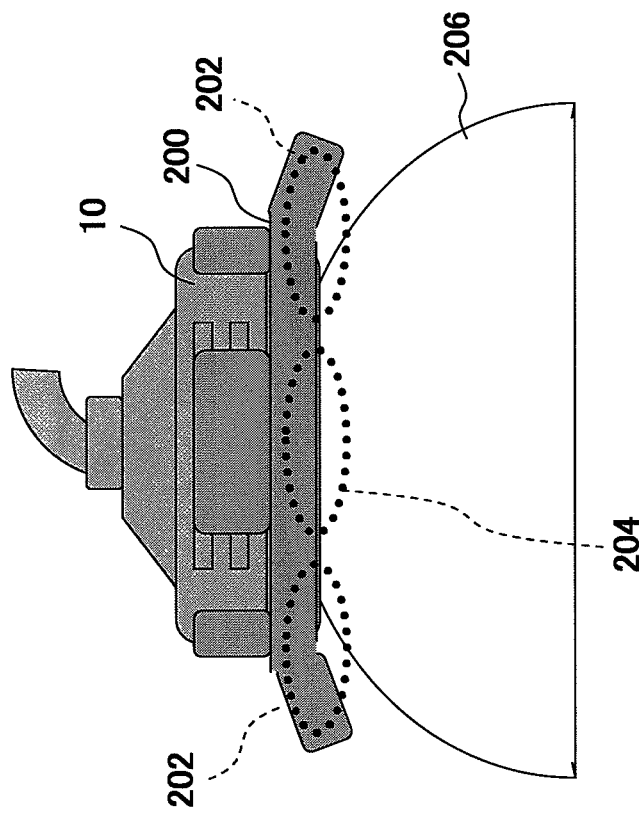
(b)

FIG. 6
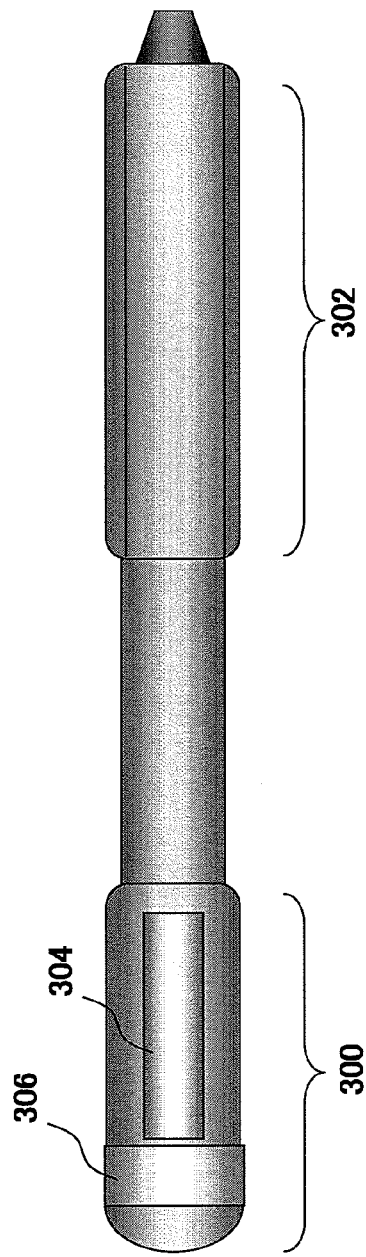
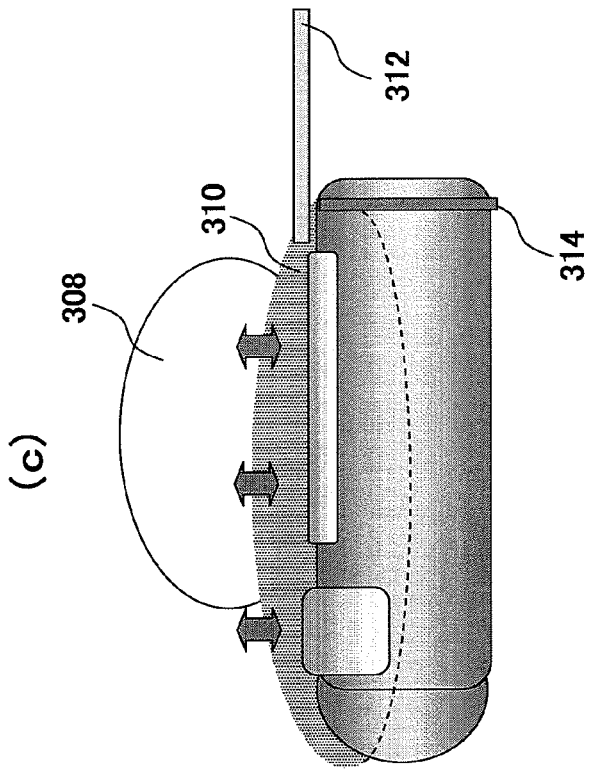
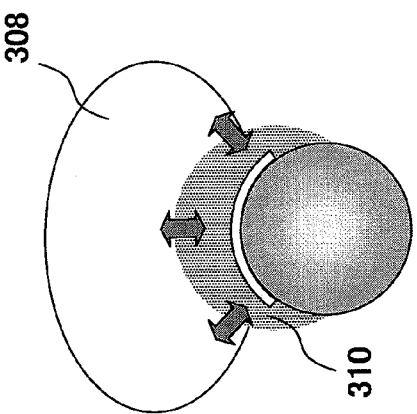

PRESSING MEMBER, ULTRASONIC PROBE AND ULTRASONIC DIAGNOSING DEVICE

TECHNICAL FIELD

The present invention relates to a pressing member, an ultrasonic probe and an ultrasonic diagnosing device, and relates to a technique of enhancing the precision of an elastic image representing hardness and softness of a biomedical tissue of a subject by pressing the subject.

BACKGROUND ART

An ultrasonic diagnosing device is a device for repetitively transmitting ultrasonic waves at a time interval to a subject through a probe which is contacted with the subject, receiving a time-series reflection echo signal emitted from the subject, and achieving a grayscale tomogram, for example, a monochromatic B mode image on the basis of the reflection echo signal.

There has been proposed a technique of measuring the displacement of a biomedical tissue of a subject on the basis of the time-series reflection echo signal emitted from the subject, acquiring elastic information such as hardness, softness, strain, elasticity modulus, etc. of the biomedical tissue from the measured displacement and constructing a color elastic image from the acquired elastic information in the ultrasonic diagnosing device as described above (for example, see Patent Document 1).

Patent Document 1: JP-2005-66041

However, when uniformity of stress field generated in the tissue is low, the pressed tissue is pushed out into a press-weak region. This being pushed out prevents the stress from coming down to a deep region, which may cause occurrence of noises in the elastic image. Therefore, even when uniform press is applied, the region area of the elastic image which can be normally acquired is reduced, and thus the efficiency of the image diagnosis is lowered.

In (Patent Document 1), a flat-plate type press plate is mounted on a probe so that a broad region of the subject can be uniformly pressed. However, the same problem may occur in the end region of the press plate, and it is still required to make an effort of further improving the press plate.

Therefore, the present invention has an object to achieve an elastic image having high precision by enabling a subject to be uniformly pressed.

DISCLOSURE OF THE INVENTION

In order to solve the problem, a pressing member according to the present invention is constructed as follows. That is, the pressing member that is detachably mounted in an ultrasonic probe to press a subject is provided with a first member for transferring pressing force in a direction parallel to a pressing direction to the subject and a second member for transferring pressing force in a direction different from the pressing direction.

In order to solve the problem, an ultrasonic probe according to the present invention is constructed as follows. That is, the probe is equipped with a pressing portion for pressing a subject, and the pressing portion has a first member for transferring pressing force in a direction parallel to the pressing direction to the subject, and a second member for transferring the pressing force in a direction different from the pressing direction.

Furthermore, in order to solve the problem, an ultrasonic diagnosing device of the present invention is constructed as follows. That is, the ultrasonic diagnosing device is equipped with an ultrasonic probe having an ultrasonic transmission/reception face for repetitively transmitting ultrasonic waves to a subject and receiving time-series reflection echo signal corresponding to the transmission of the ultrasonic waves, a tomogram constructing portion for constructing a tomogram of a biomedical tissue of the subject on the basis of the time-series reflection echo signal, an elastic image constructing portion for measuring the displacement of the biomedical tissue of the subject on the basis of the time-series reflection echo signal to acquire elastic information and construct an elastic image, and a display portion for displaying an image constructed by the tomogram constructing portion and the elastic image constructing portion, wherein the ultrasonic probe is equipped with a pressing portion for pressing a subject, and the pressing portion has a first member for transferring pressing force in a direction parallel to the pressing direction to the subject, and a second member for transferring the pressing force in a direction different from the pressing direction.

According to the pressing member, the ultrasonic probe and the ultrasonic diagnosing device of the present invention, the subject can be uniformly pressed, and thus a high-precision elastic image can be achieved. Accordingly, the image diagnosis can be efficiently performed.

BRIEF DESCRIPTION OF THE DRAWINGS

FIG. 1B is a diagram showing a state that the pressing plate according to the first embodiment of the present invention is mounted on a probe.

FIG. 1C is a diagram showing another possible structure of the pressing plate according to the first embodiment of the present invention.

FIG. 1D is a diagram showing another possible shape of the pressing plate according to the first embodiment of the present invention.

FIG. 4 is a diagram showing a fifth embodiment according to the present invention.

FIG. 6 is a diagram showing a seventh embodiment of the present invention.

BEST MODE FOR CARRYING OUT THE INVENTION

Figure 10:
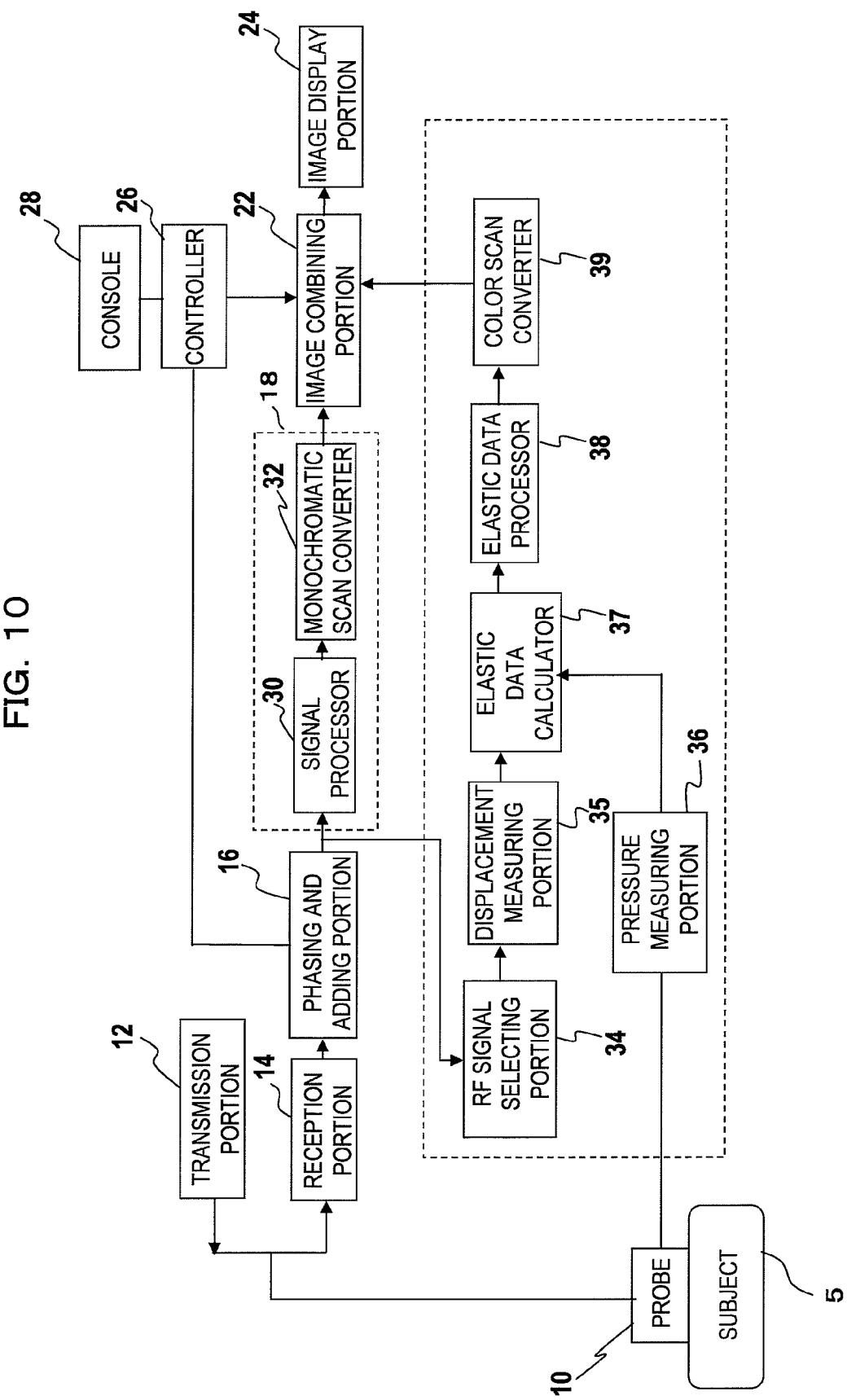
FIG. 10 is a diagram showing the overall construction of an embodiment of the present invention.

First, examples of an ultrasonic probe (hereinafter referred to as "probe") and an ultrasonic diagnosing device to which the present invention is applied will be described with reference to FIG. 10. FIG. 10 is a block diagram showing an example of the construction of the probe and the ultrasonic diagnosing device to which the present invention is applied.

As shown in FIG. 10, an ultrasonic diagnosing device 1 is equipped with a probe 10 which is used in contact with a subject 5, a transmission portion 12 for repetitively transmitting ultrasonic waves to a subject through the probe 10 at a time interval, a reception portion 14 for receiving a time-series reflection echo signal occurring from the subject, and a phasing adding portion 16 for phasing and adding the received reflection echo signal to generate RF signal frame data in time-series.

There are further provided a tomogram constructing portion 18 for constructing a grayscale tomogram of the subject, for example, a monochromatic tomogram on the basis of the RF signal frame data from the phasing and adding portion 16, and an elastic image constructing portion 20 for measuring the displacement of the biomedical tissue of the subject from the RF signal frame data of the phasing and adding portion 16 to achieve elastic data and constructing a color elastic image. An image combining portion 22 for combining the monochromatic tomogram and the color elastic image and an image display portion 24 for displaying the combined composite image are provided.

The probe 10 is formed by arranging an acoustic lens and plural transducers, and has a function of performing electrical beam-scanning to transmit/receive ultrasonic waves to/from the subject through the transducers. Furthermore, the probe 10 is used under the state that the pressing plate is mounted on the probe, or used under the state that the probe 10 is equipped with the pressing plate.

The transmission portion 12 has a function of generating a wave transmitting pulse for driving the probe 10 to generate ultrasonic waves, and also setting the convergent point of the transmitted ultrasonic waves to some depth. Furthermore, the reception portion 14 amplifies the reflection echo signal received in the probe 10 by a predetermined gain to generate an RF signal, that is, a wave reception signal.

The phasing and adding portion 16 receives the RF signal amplified in the reception portion 14 to control the phase, and forms ultrasonic beams for one point or plural convergent points to generate RF signal frame data.

The tomogram constructing portion 18 is configured to contain a signal processor 30 and a monochromatic scan converter 32. Here, the signal processor 30 receives the RF signal frame data from the phasing and adding portion 16 and executes signal processing such as gain compensation, log compression, wave detection, edge enhancement, filter processing, etc. to achieve tomogram data. The monochromatic scan converter 32 is configured to contain an A/D converter for converting tomogram data from the signal processor 30 to a digital signal, a frame memory for storing plural converted tomogram data in time-series, and a controller. The monochromatic scan converter 32 achieves as one image tomographic frame data in the subject which are stored in the frame memory by the controller, and converts the achieved tomographic frame data to a signal to be read out in synchronism with television.

Furthermore, the elastic image constructing portion 20 is constructed to contain an RF signal selecting portion 34, a displacement measuring portion 35, a pressure measuring portion 36, an elastic data calculator 37, an elastic signal processor 38 and a color scan converter 39, and it is provided at the rear stage of the phasing and adding portion 16 while branched from the phasing and adding portion 16.

The RF signal selecting portion 34 is configured to contain a frame memory and a selecting portion. The RF signal selecting portion 34 stores the plural RF signal frame data from the phasing and adding portion 16 into the frame memory, and selects a pair of, that is, two RF signal frame data from the stored RF signal frame data group through the selecting portion. For example, the RF signal selecting portion 34 successively stores into the frame memory the RF signal frame data which are generated from the phasing and adding portion 16 in time-series, that is, on the basis of the frame rate of the image, and selects the presently stored RF signal frame data (N) as first data in accordance with an instruction from the controller 26, and at the same time selects one RF signal frame data (X) from RF signal frame data group (N-1, N-2, N-3, . . . , N-M) which were stored in past times. Here, N, M, X represent index numbers allocated to the RF signal frame data, and they are assumed to be natural numbers.

The displacement measuring portion 35 determines the displacement, etc. of the biomedical tissue from a pair of RF signal frame data. For example, the displacement measuring portion 35 executes one-dimensional or two-dimensional correlation processing on the one pair of data selected by the RF signal selecting portion 34, that is, the RF signal frame data (N) and the RF signal frame data (X) to determine a one-dimensional or two-dimensional displacement distribution concerning the displacement of the biomedical tissue corresponding to each point of the tomogram and the displacement vector, that is, the direction and the magnitude of the displacement. Here, for example, a block matching method is used for detection of the displacement vector. According to the block matching method, an image is divided to blocks each comprising N×N pixels, a block in a region of interest is noted, a block which is most approximate to the block being noted is found from a previous frame, and a sample value is determined on the basis of the block concerned by the predictive coding, that is, the difference.

The pressure measuring portion 36 measures and estimates the pressure in the body cavity of a diagnosis site of the subject 5. For example, a pressure measuring portion having a pressure sensor is secured to the probe 10 or the pressing plate which is used in contact with the surface of the body of the subject, and a stress distribution is applied to the inside of the body cavity of the diagnosis site of the subject by pressurizing or reducing the pressure of the head of the probe 10 and the pressing plate. At this time, the pressure sensor measures and holds the pressure applied to the surface of the body by the probe head and the pressing plate at any time phase.

The elastic data calculator 37 calculates the strain or elasticity modulus of the biomedical tissue corresponding to each point on the tomogram on the basis of the measurement value, for example, the displacement vector from the displacement measuring portion 35 and the pressure value from the pressure measuring portion 36, and generates an elastic image signal, that is, elastic frame data on the basis of the strain or the elasticity modulus.

At this time, the data of the strain is calculated by spatially differentiating the movement amount, that is, the displacement of the biomedical tissue. The data of the elasticity modulus is calculated by diving the variation of the pressure by the variation of the movement amount. For example, when the displacement measured by the displacement measuring portion 35 is represented by $\Delta L$ and the pressure variation measured by the pressure measuring portion 36 is represented by $\Delta P$, the strain (S) can be calculated by spatially differentiating $\Delta L$, and thus it is calculated by using the equation of $S=\Delta L/\Delta X$. Furthermore, Young's modulus is known as the elasticity modulus corresponding to the strain, and the Young's modulus $Ym$ is calculated according to the equation of $Ym=(\Delta P)/(\Delta L/L)$. That is, the Young's modulus corresponds to the ration of the simple pressure applied to an object and the strain per unit length in the pressure applying direction. The elasticity modulus of the biomedical tissue corresponding to each point of the tomogram is determined from this Young's modulus, and thus the two-dimensional elastic image data can be sequentially achieved.

The elastic data processor 38 is configured to contain a frame memory and an image processor, and it stores into the frame memory elastic frame data which are output from the elastic data calculator 37 in time-series, and executes image processing on the stored frame data through the image processor in response to an instruction from the controller 26.

The color scan converter 39 executes the conversion to hue information on the basis of the elastic frame data from the elastic data processor 38. That is, it executes the conversion to light's three primary colors, that is, red (R) green (G), blue (B) on the basis of the elastic frame data. For example, elastic data having large strain is converted to a red color code, and elastic data having small strain is converted to a blue color code.

In the ultrasonic diagnosing device of the present invention, an accommodating portion for accommodating at least one pressing plate which is detachably mounted on the probe described below is provided in the neighborhood of a probe holder or to the side surface of the device or the like, for example. The pressing plate accommodating portion is designed to have a shape like a basket or box or a shape like a hook which is inserted through a hole portion of the pressing plate described later to hold the pressing plate, whereby the pressing member can be taken in and out freely.

Figure 11:
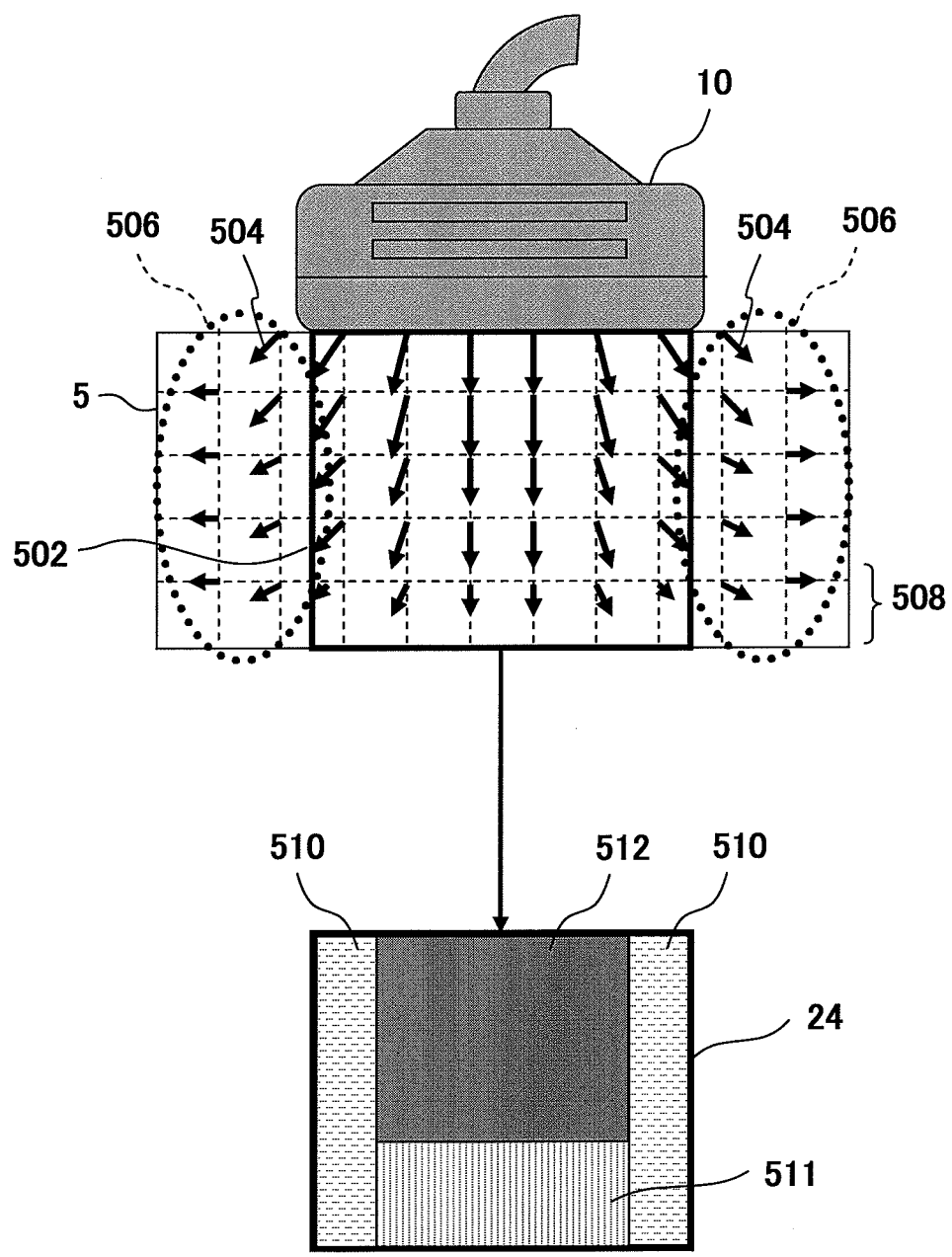
FIG. 11 is a diagram showing a prior art.

In the image pickup operation of an elastic image by using the ultrasonic diagnosing device as described above, when uniformity of a stress field generated in the tissue is low, the pressed tissue is pushed out into a press-weak area, and noise may occur in the elastic image. This phenomenon will be described with reference to FIG. 11. FIG. 11 is a diagram showing a model in which a target having uniform hardness is pressed by using the probe 10. The contact area of the probe 10 to the subject, that is, the pressing area is small, and thus a displacement vector faces the outside in a region 506. Accordingly, the pressed tissue at the center portion is pushed out to the non-pressed region, so that noises are induced at both the side regions 510 of the elastic image displayed on the image display portion 24. Furthermore, the stress to be applied to a deep region is prevented from coming down to the deep region by the above fleeing, so that noise is induced in a deep region 511 of the elastic image. Therefore, even when uniform pressing is applied, the area of the region in which a normal elastic image 512 can be achieved is reduced. That is, the normal region of the elastic image displayed on the image display portion 24 is narrowed. The above-described problem associated with the elastic image is solved by the pressing member, the probe and the ultrasonic diagnosing device of the present invention described below, and some embodiments will be described in detail.

(First Embodiment)

A first embodiment according to the present invention will be described. First, the shape of the pressing member of this embodiment will be described. The pressing member of this embodiment is characterized by comprising a first member for transferring pressing force in a direction parallel to the pressing direction to the subject, and a second member for transferring pressing force in a direction different from the pressing direction.

The second member is preferably designed as follows. That is, it is formed so as to extend to the edge portion of the first member. Furthermore, it is designed so that the transferring direction of the pressing force faces the center portion side of the first member so as to intersect with the pressing direction. Furthermore, considering the perspective of the subject, the second member is formed so as to press a part of the subject pressed by the first member so that the part of the subject is prevented from being pushed out in a direction different from the pressing direction.

Furthermore, considering the perspective of the contact face of the pressing member to the subject, the first member has a first face vertical to the pressing direction, and the second member has a second face perpendicular to the direction different from the pressing direction. That is, the contact face is formed so that the vertical direction of at least a partial face thereof is different from the vertical direction of the other remaining face thereof.

An example in which a plate-shaped member is used as the pressing member will be described below, and thus the pressing member will be referred to as pressing plate.

Figure 1A:
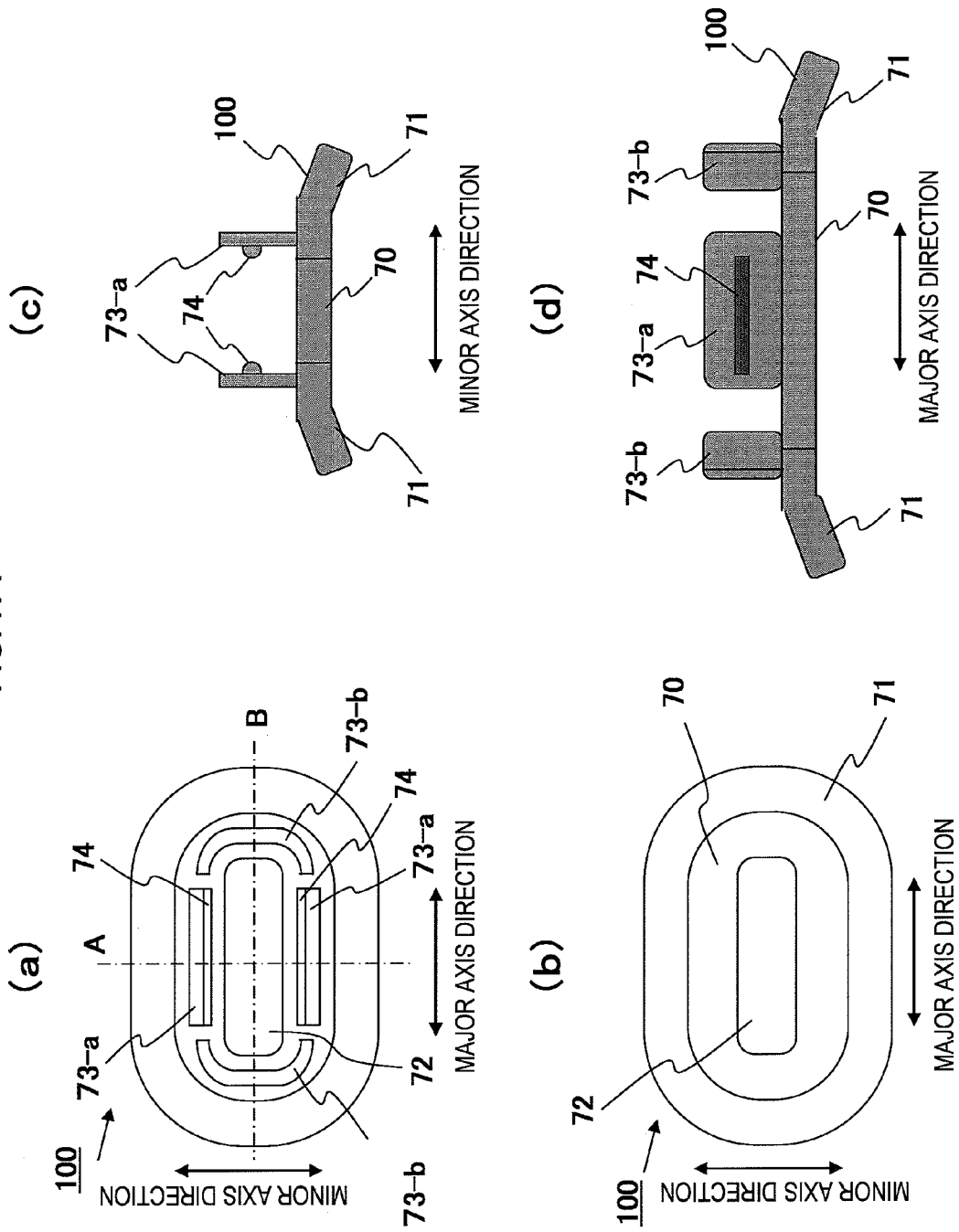
FIG. 1A is a diagram showing the shape of a pressing plate according to a first embodiment of the present invention.

FIG. 1A shows an example of the pressing plate of this embodiment. FIG. 1A(*a*) is a top view of the pressing plate 100, FIG. 1A(*b*) is a bottom view of the pressing plate 100, FIG. 1A(*c*) is a cross-sectional view of the pressing plate 100 taken at a position indicated by a one-dotted chain line A when viewed in the minor axis direction, FIG. 1A(*d*) is a cross-sectional view of the pressing plate 100 at a position indicated by a one-dotted chain line when viewed in the major axis direction. The pressing plate 100 is formed of material such as plastic, polyvinyl based material or the like, for example. The pressing plate 100 is designed to be larger in dimension than the probe 10 in the major and minor axes of the probe 10 so that the pressing plate 100 can press the subject over a broader area than the ultrasonic wave transmission/reception face 11 of the probe 10, and the edge portion of the pressing plate 100 is designed in a substantially rectangular shape or the like so that the four corners thereof are rounded. The shape of the edge portion of the pressing plate may be set to another shape, and for example it may be circular, elliptic or polygonal.

The lower surface of the pressing plate is the surface which comes into contact with the body surface of the subject. As shown in FIG. 1A(*b*), the lower surface of the pressing plate 100 has a flat face (first face) 70 at the center portion thereof, and a slant face 71 (second face) that extends to the edge portion of the flat face 70 and intersects with the flat face 70. That is, the slant face 71 is designed to be oblique to the flat face 70 so that the vertical direction (the direction of the normal line) of the slant face 71 intersects with the vertical direction (the direction of the normal line) of the flat face 70 (that is, the slant face 71 faces the center portion side of the lower surface of the pressing plate). This design makes the lower surface of the pressing plate in a concave shape. The slant face 71 may be flat or concaved. Or, it may contain a flat face and a concave face in mixture.

The length in the major direction of the flat face 70 of the pressing plate 100 is set to be equal to or longer than the length in the major direction of the probe 10. The intersection angle between the slant face 71 and the flat face 71 is set in the range from 90 to 180 degrees. The width of the slant face 71 may be set to several mm to several cm which is in the same level as the width in the minor direction of the probe 10, however, it may be set in accordance with the site of the subject. Likewise, the width of the flat face 70 from the side surface of the probe 10 to the slant face 71 may be set in the range from several mm to several cm, however, it may be set in accordance with the site of the subject.

The slant face 71 may be formed at at least a part of the edge portion of the pressing plate 100, however, it is preferable that the slant face 71 is formed on the whole periphery of the edge portion of the pressing plate 100. Particularly, in the case of the pressing plate 100 shown in FIG. 1A, the slant face 71 is formed at both the sides in each of the minor axis direction and the major axis direction along each axis direction, and this it is suitable for a linear type probe. That is, the slant face 71 formed along the minor axis direction of the pressing plate 100 is formed obliquely to the flat face 70 so as to face the center portion side in the major axis direction of the pressing plate 100, and the slant face 71 formed along the major direction of the pressing plate 100 is formed obliquely to the flat face 70 so as to face the center portion side in the minor axis direction of the pressing plate 100. The slant face 71 may be formed along any one of the minor axis direction and the major axis direction of the pressing plate 100, or may be formed at only one side in one axis direction.

In the above embodiment, the lower surface of the pressing plate has the flat face and the slant face. However, it may be designed in other shapes. For example, the lower surface of the pressing plate may be designed in a concaved shape at least a part of which varies smoothly. That is, at least one of the flat face 70 and the slant face 71 may be designed to have a concave shape at least a part of which varies smoothly. Conversely, it may be designed to have a convex shape at least a part of which varies smoothly. That is, at least one of the flat face 70 and the slant face 71 may be designed to have a convex shape at least a part of which varies smoothly. FIG. 1D shows these examples. In the example of each pressing plate shown in FIG. 1D, the display of the fixing portion mounted on the upper surface is omitted, and the cross-section in the major axis direction is shown when viewed in the major axis direction. With respect to a pressing plate 100-1 of FIG. 1D(*a*), only the slant face 71 has a smooth concave shape. With respect to a pressing plate 100-2 of FIG. 1D(*b*) both the flat face 70 and the slant face 71 have a smooth concave shape and they are smoothly connected to each other, thereby forming a smooth concave shape as a whole. With respect to a pressing plate 100-3 of FIG. 1D(*c*), only the slant face 71 has a smooth convex shape. With respect to a pressing plate 100-4 of FIG. 1D(*d*), both the flat face 70 and the slant face 71 have a smooth convex shape, and they are smoothly connected and form a smooth convex shape as a whole. In any case, the same is applied to the minor axis direction of the pressing plate.

Furthermore, a hole portion 72 is provided to a part of the pressing plate 100 so that an acoustic lens, that is, an ultrasonic wave transmission/reception face 11 of the probe 10 can be disposed. The probe 10 transmits/receives ultrasonic waves through this hole portion 72 to/from the subject. That is, it is configured so that the ultrasonic wave transmission/reception face 11 of the probe 10 is brought into direct contact with the subject through the hole portion 72. The hole portion in which the ultrasonic wave transmission/reception face is disposed is preferably formed substantially at the center of the pressing plate, and the hole portion 72 is formed substantially at the center of the flat portion 70 in the pressing plate 100 shown in FIG. 1A. The surface of the ultrasonic wave transmission/reception face 11 may also serve as at least a part of the flat face 70. That is, the pressing plate 100 may be constructed so that the ultrasonic wave transmission/reception face 11 constitutes a part of the flat face 70 of the pressing plate 100. Furthermore, by setting the ultrasonic wave transmission/reception face 11 to the flat face 70, the pressing plate 100 which does not have the flat face 70, but has only the slant face 71 may be constructed.

The upper surface of the pressing plate is equipped with a fixing portion through which the pressing plate is detachably mounted on the probe. This fixing portion has at least one side surface fixing portion for fixing the arrangement position in the side surface direction of the probe while sandwiching the probe therein. At least one side surface fixing portion has a fitting portion which is fitted to at least a part of the side surface of the probe to fix the arrangement position in the insertion direction of the probe. By the fixing portion having the above structure, the relative position in the minor axis direction and the major axis direction between the probe and the pressing plate is fixed by the side surface fixing portion, and the relative position in the probe insertion direction between the probe and the pressing plate is fixed by the fitting portion, whereby the pressing plate is mounted on the probe.

In the example of the fixing portion shown in FIG. 1A, a pair of counter plates 73 as the side surface fixing portion are formed and disposed in each of the major axis direction and the minor axis direction while the hole portion 72 in which the probe 10 is disposed is sandwiched therebetween, and a projecting portion 74 as a fitting portion is formed at the hole portion 72 side of each of the pair of counter plates 73-*a*. The two pairs of counter plates 73 clamp and hold the probe 10 disposed in the hole portion 72 in the major axis direction and the minor axis direction, whereby the relative positions in the minor axis direction and the major axis direction between the probe 10 and the pressing plate 100 are fixed. Furthermore, the projecting portions 74 are fitted to recesses 75 of the probe 10, whereby the relative position in the probe insertion direction between the probe 10 and the pressingplate 100 is fixed. If each counterplate 74 is formed of a material such as plastic, polyvinyl or the like, it would be easy to slightly deform the counter plates by the force having the same level as human power to fit the projecting portions 74 to the recesses 75 of the probe 10. The pressing plate 100 can be easily mounted on and detached from the probe 10 by the fixing portion having the structure as described above.

The back surface of each counter plate may be provided with an antiskid grip to be gripped by a hand. FIGS. 1C(*a*) (*b*) show an example of the structure of the antiskid grip. FIGS. 1C(*a*) (*b*) are diagrams showing the probe 10 on which the pressing plate 100 is mounted when the probe 10 is viewed in the major axis direction and in the minor axis direction, respectively. An examiner grips the antiskid grips 76 and presses the subject through the pressing plate 100. In order to make it easy to grasp the antiskid grips 76, the back surfaces of the counter plates 73 may be designed to have a concave shape 77 which is matched with the shape of a finger. The antiskid grip 76 may be provided to the back surface of at least one counter plate. Furthermore, the back surface of the counter plate may be designed to have a concave shape 77 with omitting the antiskid grip 76.

Furthermore, the conventional probe is provided with a projecting portion for making the ultrasonic wave scan direction recognizable, and the fixing portion of the pressing plate may have a structure which enables an examiner to grasp the projecting portion even under the state that the pressing plate is mounted on the probe. The example of this structure is shown in FIG. 1C(*c*) (*d*). FIG. 1C(*c*) is a diagram showing an example in which one of the counter plates has a structure covering the projecting portion 77, and is views of the probe 10 in which the pressing plate 100 is mounted, the views being taken in the major axis direction (upper diagram) and in the minor axis direction (lower diagram), respectively. In this structure, a raised portion 78 occurs at the outside of the counter plate 73 covering the projecting portion 77, and thus the examiner can recognize this raised portion 78 as a substitute of the projecting portion 77. Furthermore, FIG. 1C(*d*) shows a diagram showing a structure in which the counter plate 73 avoids the projecting portion 77, and shows the probe 10 having the pressing plate 100 mounted thereon when the probe 10 is viewed in the major axis direction (upper diagram) and in the minor direction (lower diagram). In this structure, the counter plate 73 avoids the projection portion 77, and holds the side surface of the probe at only the portion between the projection portion 77 and the pressing plate 100. Therefore, the examiner can directly recognize the projection portion 77 of the probe.

At least a part of the pressing plate is constructed by a deformable member, and at least a part of the slant face of the edge portion is configured to be deformable to a desired shape. Copper, iron, aluminum or the like may be used as the deformable material. By forming the pressing plate of the deformable member, the edge portion of the pressing plate can be deformed so that the slant angle of the edge portion is matched with the shape of the body surface of the subject. By using the pressing plate as described above, the examiner can deform the surface of the lower surface of the pressing plate in conformity with the shape of the body surface of the subject, whereby the body surface of the subject can be effectively pressed. Particularly, by adopting the material (plastic, foamed polystyrene or the like) or the structure (the boundary portion between the flat portion and the edge portion is thinned) that can be easily deformed by minute force having the same level as pressing and in which the deformation is within the plastic deformation range, the lower surface shape of the pressing plate and the slant angle of the slant face of the edge portion is automatically deformed simultaneously with the pressing while following the shape of the body surface of the subject, and also the shape of the lower surface of the pressing plate is returned to the original one simultaneously with release of the pressing. As a result, even the same pressing plate can be flexibly adapted to different body surface shapes, so that the burden of exchanging the pressing plate can be reduced, and further the efficiency of the image diagnosis can be enhanced.

Furthermore, the edge portion (second member) having the slant face may be configured to be detachable from the flat portion (first member) having the flat face. Plural kinds of edge portions having different slant faces are prepared in advance, and an edge portion having a slant face conformed to the body surface shape of the subject is selected and mounted to the flat portion. By using the thus-constructed pressing plate, the pressing plate can be flexibly adapted to the different body surface shapes of the subject.

Next, the state that the pressing plate is detachably mounted on the ultrasonic wave transmission/reception surface side of the probe will be described. FIG. 1B shows an example in which the pressing plate 100 shown in FIG. 1A is mounted on the probe 10. FIG. 1B(*a*) is a view taken in the major axis direction, FIG. 1B(*b*) is a cross-sectional view in the minor axis direction at a position indicated by a one-dotted chain line when viewed in the minor axis direction, FIG. 1C(*c*) is a perspective view showing the lower surface of the pressing member 100 and the ultrasonic wave transmission/reception face 11. The two pairs of counter plates 73 in the minor axis direction and in the major axis direction sandwich the probe 10 among them to fix the relative positions in the respective directions so that the ultrasonic wave transmission/reception face 11 is disposed in the hole portion 72 and slightly projects from the lower face of the pressing plate 100. The projecting portions 74 at the inside of the counter plates 73-*a* are fitted to the recesses 75 of the probe 10, whereby the relative position in the insertion direction between the probe and the pressing plate is fixed. The pressing plate 100 is fixed to the probe 10 as described above. The examples of the pressing plate shown in FIGS. 1C, 1D can be mounted to the probe 10 in the same manner.

Under the state that the pressing plate 100 is mounted on the probe 10, the vertical direction of the surface of at least a part of the lower surface of the pressing plate 100 is different from the vertical direction of the ultrasonic wave transmission/reception face 11. For example, the lower surface of the pressing plate 100 has the flat face 70 along the ultrasonic wave transmission/reception face 11 and the slant face 71 having an angle different from the flat face 70 with respect to the ultrasonic wave transmission/reception face 11. In the example of FIG. 1B, the slant face 71 is inclined to the center portion side of the ultrasonic wave transmission/reception face 11 with respect to the flat face 70 so that the vertical direction of the slant face 71 intersects with the vertical direction of the flat face 70. Furthermore, the flat face 70 is parallel to the ultrasonic wave transmission/reception face 11. In the foregoing description, the pressing plate is detachably mounted on the probe. However, the probe may be configured to be equipped with each pressing plate described above in advance.

Figure 2:
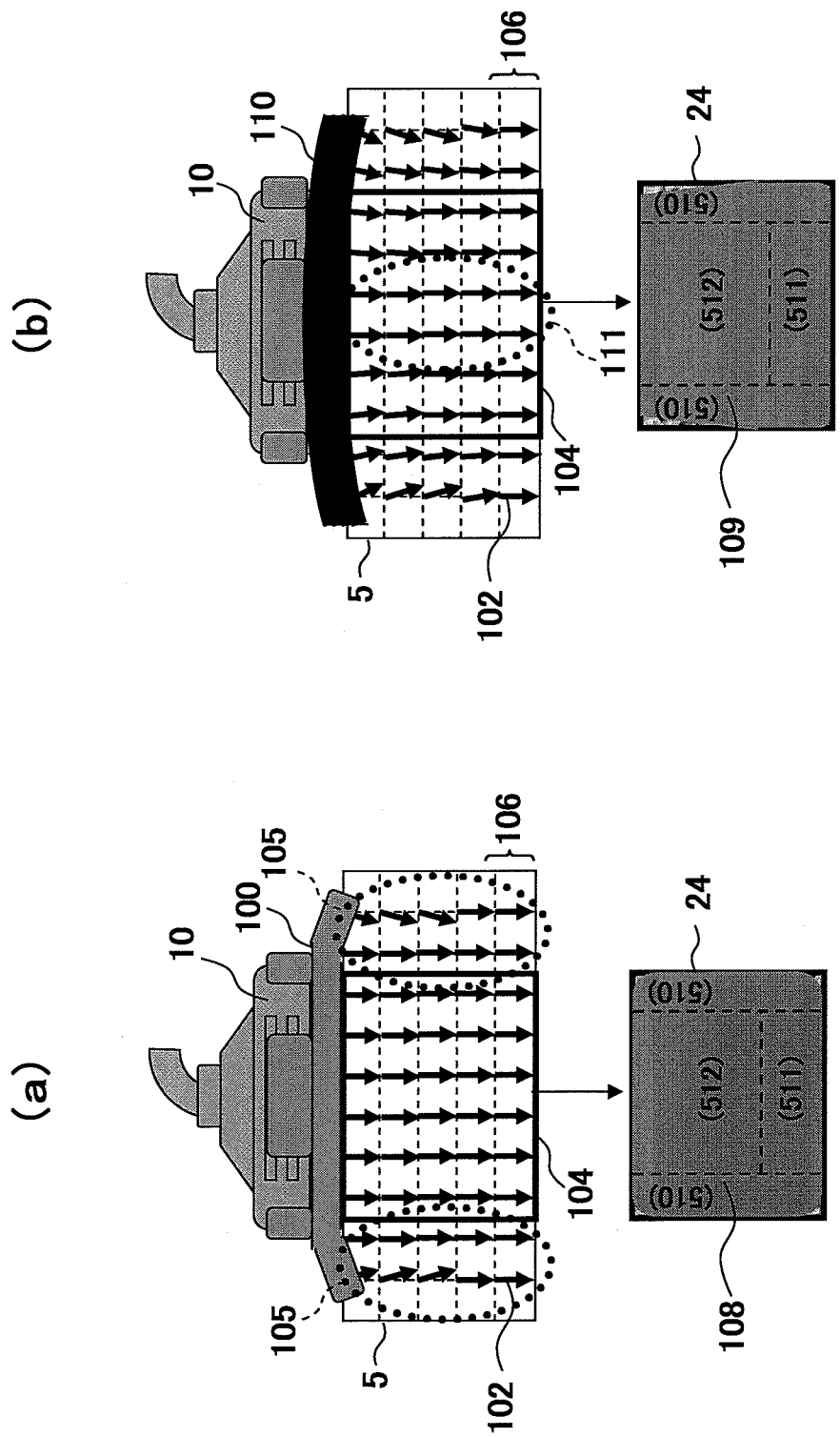
FIG. 2 is a diagram showing first and second embodiments of the present invention.

Next, the aspect of the variation of the tissue of the subject when the subject 5 is pressed by using the pressing plate 100 as described above will be described with reference to FIG. 2(*a*). FIG. 2(*a*) shows the probe 10 having the pressing plate 100 mounted thereon when the probe 10 is viewed in the major direction, and shows the aspect of the displacement vector in a pressed tissue of the subject 5.

By using the pressing plate 100, the subject 5 is pressed vertically to the surface with which the probe 10 is in contact together with the acoustic lens as the ultrasonic wave transmission/reception face 11, the strain and the elasticity modulus of the biomedical tissue corresponding to each point on the tomogram are calculated from the displacement vector indicated by an arrow 102 which is calculated from the reflection echo signal received by the probe 10, and the pressure value from the pressure measuring portion 36, and then the elastic image signal, that is, the elastic frame data are generated on the basis of the strain and the elasticity modulus. On the basis of the elastic frame data, the elastic image corresponding to the region 104 is displayed on the image display portion 24. This subject 5 is assumed to have uniform hardness.

In this embodiment, the surface area of the subject 5 under press is more increased as compared with the case where the subject 5 is pressed by only the probe 10 by using the pressing plate 100. Furthermore, the shape of the pressing plate 100 is set so that the center portion thereof is set to a flat shape and the edge portion thereof has a shape facing the inside (that is, the center portion side of the probe 10). Therefore, the displacement vector faces the inside (that is, the center portion side of the probe 10) in the region 105 of the edge portion, and it faces the same direction as the pressing direction in the deep region 106. The region of the center portion is pressed inwardly (that is, to the center portion side of the probe 10) by the displacement vector 102 of the region 105 of the edge portion, and thus the tissue is suppressed from fleeing outwardly (to the edge portion side of the probe 10) as shown in FIG. 11, so that the stress effectively comes down to the deep portion.

Accordingly, the pressing plate 100 keeps the pressing direction to be vertical to the surface with which the probe 10 comes into contact, and also the edge portion region is pressed to the center portion side of the probe 10, whereby the region of the elastic image 108 displayed on the image display portion 24 is broadened in the major axis direction of the probe 10. Furthermore, stress which is sufficient to achieve the elastic image 108 can be applied at the deep portion, and thus an elastic image 108 which is broad in the depth direction can be achieved. In order to make the difference from FIG. 11 easily understandable, the partial regions corresponding to the partial regions 510, 511 and 512 of the elastic image of FIG. 11 are represented by the same region numbers while the region numbers are written in parentheses. That is, by using the pressing plate of this embodiment, the normal elastic image can be achieved in all the regions 510 to 512. Accordingly, the elastic image which is normally displayed is broadened and thus the image diagnosis can be efficiently performed.

(Second Embodiment)

Next, a second embodiment of the present invention will be described with reference to FIG. 2(b). FIG. 2(b) shows the probe 10 on which the pressing plate 100 is mounted when the probe 10 is viewed in the major axis direction. A pressing plate 110 having an arcuate lower surface is detachably secured to the ultrasonic wave scanning face side of the probe 10. The difference from the first embodiment resides in that the pressing plate 110 has an arcuate shape.

The arcuate pressing plate 110 is designed so that the slant angle gradually grows steeper to the subject side as the position shifts to the edge portion, and the contact surface with the subject 5 has a concave shape. For example, the pressing plate has a concave curve as shown in FIG. 1D(b). Therefore, the displacement vector 102 of the edge portion is inclined to the inside (that is, the center portion side of the probe 10) as compared with the displacement vector 102 at the center portion.

As described above, the region 111 at the center portion is pressed inwardly (that is, to the center portion side of the probe 10) by the displacement vector 102 of the regions of the edge portions. Therefore, in the region 111 at the center portion, the displacement vector 102 is kept vertical to the ultrasonic wave transmission/reception face 11 at the shallow portion (that is, the portion near to the probe 10) and the deep portion (that is, the portion far away from the probe 10). Furthermore, in the regions other than the region 111 of the center portion, the displacement vector 102 in the pressing direction gradually becomes vertical to the ultrasonic wave transmission/reception face 11 as the position approaches to the region 106 of the deep portion.

Accordingly, as in the case of the first embodiment, the pressing direction is kept to be vertical to the surface with which the probe 10 is in contact over a broad range, whereby the normal region of the elastic image 109 displayed on the image display portion 24 is broadened in the major axis direction and the deep direction of the probe 10. In order to make the difference from FIG. 11 easily understandable, the partial regions corresponding to the partial regions 510, 511 and 512 of the elastic image of FIG. 11 are represented by the same region numbers while the region numbers are written in parentheses. Accordingly, the normally displayed elastic image is broader, and thus the image diagnosis of the inside of the subject 5 can be efficiently performed.

The probe may be designed to be equipped with the pressing plate of this embodiment in advance as in the case of the first embodiment.

(Third Embodiment)

Figure 3:
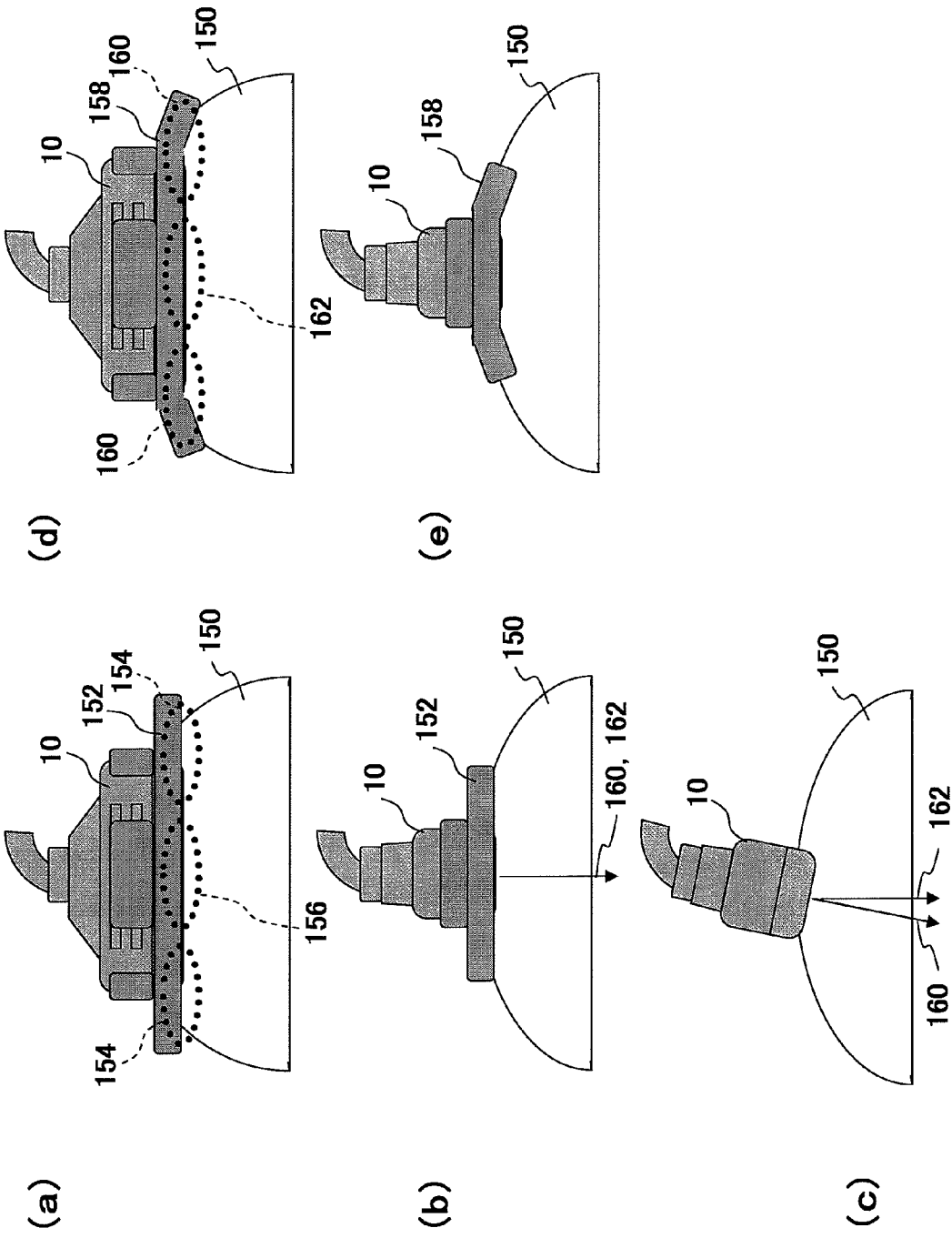
FIG. 3 is a diagram showing third and fourth embodiments of the present invention.

Next, a third embodiment of the present invention will be described with reference to FIGS. 3(a) (b). FIG. 3(a) shows a pressing plate 152 for pressing the subject 5 and the probe 10 when they are viewed in the major axis direction. FIG. 3(b) shows the pressing plate 152 and the probe 10 when they are viewed in the minor axis direction. The flat-plate type pressing plate 152 is detachably secured to the ultrasonic wave scanning face side of the probe 10. The difference from the first embodiment and the second embodiment resides in that the pressing plate 152 is of a flat-plate type and the size of the pressing plate is suitable for the site being examined of the subject 5.

An observation site 150 of the subject 5 is abreast, for example. The pressing plate 152 has the size suitable for the observation site 150, and the surface area of the pressing face is larger than the case where the observation site 150 is pressed in the major axis and minor axis directions by only the probe 10.

When no pressing plate is provided, there is a case where the ultrasonic wave irradiation direction of the probe 10 and the pressing direction are not coincident with each other. FIG. 3(c) shows the probe 10 under the state that no pressing plate is provided when the probe 10 is viewed in the minor axis direction. The width in the minor axis direction of the probe 10 is equal to about 1 cm, and the pressing face is not fixed, so that the ultrasonic wave irradiation direction 160 is fluctuated, so that the ultrasonic wave irradiation direction 160 and the pressing direction 162 are hardly coincident with each other. Therefore, according to this embodiment, by increasing the surface area of the pressing face as shown in FIG. 3(b), the direction of pressing the subject 5 by the probe 10 is set to be vertical to the ultrasonic wave transmission/reception face 11, and the subject 5 is pressed so that the ultrasonic wave scanning direction 160 and the pressing direction 162 are coincident with each other. Accordingly, the elastic image can be stably achieved.

The probe may be configured to be equipped with the pressing plate of this embodiment as in the case of the first embodiment.

(Fourth Embodiment)

With respect to the pressing plate 152 of the third embodiment shown in FIGS. 3(a) (b), the pressing force is strong at the center portion 156, however, the pressing force may be reduced at the edge portions 154. Therefore, the elastic image of the depth region of the center portion 156 is clearly displayed, however, the elastic image of the depth region of each edge portion 154 may be disturbed.

Therefore, a fourth embodiment as an improvement of the third embodiment will be described with reference to FIGS. 3(d)(e). FIG. 3(d) shows a pressing plate 158 for pressing the subject 5 and the probe 10 when they are viewed in the major axis direction. FIG. 3(e) shows the pressing plate 158 and the probe 10 when they are viewed in the minor axis direction.

The difference from the third embodiment resides in that the pressing plate 158 is designed in such a cup-shape as to be curved to the subject side in both the minor axis direction and the major axis direction and wrap the observation site 150. By using this pressing plate 158, the stress force is strong not only at the center portion 162, but also at the edge portions 160. This principle of pressing is identical to that of the first embodiment shown in FIG. 2(a), and the displacement vector faces the inside (that is, the center portion side of the probe 10) in the region 160 of the edge portion, and faces the same direction as the pressing direction in the deep region. Furthermore, the region 162 of the center portion is pressed inwardly (that is, to the center portion side of the probe 10) by the displacement vector 102 of the regions of the edge portions, and thus the stress loss is small, so that sufficiently large stress is applied even in the deep region. As a result, a proper elastic image can be achieved. The pressing plate 158 may be designed in a spherical shape, an ellipsoidal shape or a substantially conical shape so that the pressing plate 158 can be brought into close contact with the observation site of the subject 5 in connection with the shape of the body surface of the observation site of the subject 5.

As described above, the pressing direction is kept to be vertical to the surface with which the probe comes into contact, whereby the region of the elastic image displayed on the image display portion 24 can be broadened in the major axis direction or in the depth direction. Accordingly, the normally displayed elastic image is broadened, and thus the image diagnosis can be efficiently performed.

The probe may be configured to be equipped with the pressing plate of this embodiment in advance as in the case of the first embodiment.

(Fifth Embodiment)

Next, a fifth embodiment according to the present invention will be described with reference to FIG. 4. FIGS. 4(a)(b) shows a pressing plate 200 for pressing the subject 5 and the probe 10 when they are viewed in the major axis direction. An observation site 206 of the subject 5 corresponds to a part of the neck of the subject 5, for example. The difference from the first to fourth embodiments resides in that a deformable member 208 formed of a material which efficiently propagates ultrasonic waves therethrough is inserted between the pressing plate 200 and the observation site 206 of the subject 5.

FIG. 4(a) is a diagram for clarifying the effect of the present invention in this embodiment. When no deformable member 208 is provided as shown in FIG. 4(a), a gap occurs between the observation site 206 of the subject 5 and the pressing plate 200. Therefore, the region 204 of the center portion is normally pressed by the pressing plate 200, however, a gap occurs in the region of each edge portion, so that the region of the edge portion is not pressed in close contact with the pressing plate 200.

FIG. 4(b) shows the construction that the gap regions 202 are embedded with the deformable member 208. The deformable member 208 is formed of a gel material or the like through which ultrasonic waves are passed, and it is secured to the surface of the pressing plate 200. By using the deformable member 208, the gap regions 202 occurring in FIG. 4(a) are embedded, and the pressing plate 200 is brought into close contact with the observation site 206 of the subject 5 through the deformable member 208. Accordingly, the subject 5 can be uniformly pressed inwardly (that is, to the center portion side of the probe 10) under the state that the pressing plate 200 is brought into close contact with the subject 5. Therefore, as in the case of each of the above-described embodiments, the region of the elastic image 108 displayed on the image display portion 24 can be broadened in the depth direction. That is, even at a site which is more slender than the width of the major axis of the probe 5 like the observation site 206 of the subject 5, the elastic image which is normally displayed at the deep portion can be broadened by using the deformable member, and thus the image diagnosis can be efficiently performed.

An existing product formed of polymer gel for acoustic coupling "Sonagel" (produced by Takiron Co., Ltd.) or the like may be used as an example of the deformable member 208. Furthermore, a bag filled with liquid may be used. Still furthermore, by fixing the deformable member as described above to the pressing plate, the pressing plate and the deformable member are constructed as one unit.

(Sixth Embodiment)

Figure 5:
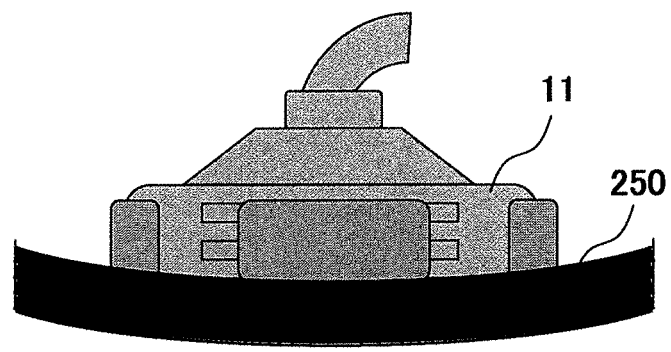
FIG. 5 is a diagram showing a sixth embodiment of the present invention.

Next, a sixth embodiment according to the present invention will be described with reference to FIG. 5. FIG. 5 shows a pressing plate 250 having a convex shape for pressing the body surface of the subject 5 and a convex type probe 11 when the pressing plate and the convex type probe are viewed in the major axis direction. The difference from the first to fifth embodiments resides in that a pressing plate 250 adapted to the convex type probe 11 as one type probe 10 is provided.

The lower surface of the pressing plate 250 has a plane which is substantially coincident with the curvature of the ultrasonic wave transmission/reception face of the convex type probe 11. For example, the pressing plate has a convex surface as shown in FIG. 1(D) (d), for example. That is, the lower surface of the pressing plate 250 as the contact surface with the subject 5 has the surface having substantially the same shape as the ultrasonic wave transmission/reception face of the convex type probe 11, and it is designed in a convex shape so as to project to the subject 5 side. Accordingly, the convex type probe 11 and the lower surface of the pressing plate 250 are brought into close contact with the subject 5 to press the subject 5, whereby the elastic image can be efficiently displayed by using even the convex type probe 11.

The probe may be configured to be equipped with the pressing plate of this embodiment in advance as in the case of the first embodiment.

(Seventh Embodiment)

Next, a seventh embodiment according to the present invention will be described with reference to FIG. 6. FIG. 6(a) is a diagram showing the outlook of a transrectal ultrasonic probe. When the examiner grips a probe grip portion 302 and inserts a body insertion portion 300 into the rectum, the ultrasonic wave transmission/reception face comes into contact with the inner surface of the rectum of the subject 5. A biplane type ultrasonic wave transmission/reception portion 304 and a ultrasonic wave transmission/reception portion 306 are disposed in the body insertion portion 300, and a monochromatic tomogram and a color elastic image are generated on the basis of reflection echo signals received from the respective ultrasonic wave transmission/reception portions. A pressing mechanism as shown in Patent Document 2 is equipped in the probe, and a switch (not shown) as an interface for operating the pressing mechanism is provided to the probe grip portion 302. The examiner may operate the switch by his/her finger with which the probe grip portion 302 is gripped, thereby controlling the pressing of the inner surface of the rectum.

Patent Document 2: WO 2004/105615

FIG. 6(b) and FIG. 6(c) show the transrectal ultrasonic probe when it is viewed in the minor axis direction and the major axis direction, respectively. In this embodiment, a bag 315 is mounted to the outside of an existing transrectal ultrasonic probe by a fixing belt 314, and liquid (water, normal saline solution or the like) is supplied/exhausted to/from the bag 315 by a pump (disposed at the outside of the subject, and not shown) connected through a tube 312 to thereby expand or contract the bag 315, whereby pressing is directly applied to the inner surface of the rectum of the subject 5.

The bag 315 which is in contact with the rectum, the prostate 308 of the subject 5 is set to a state as shown in FIG. 3(b) when the bag 315 is expanded, and it can press the target over a broad area by the ultrasonic wave transmission/reception face, so that the pressing can be efficiently performed till the deep region. Furthermore, at any position of the ultrasonic wave transmission/reception face, the bag 315 is expanded in the vertical direction (the normal-line direction) to the face concerned. Therefore, the subject 5 can be uniformly pressed at any position in any direction, and thus the uniformity of the image quality can be enhanced.

(Eighth Embodiment)

Figure 7:
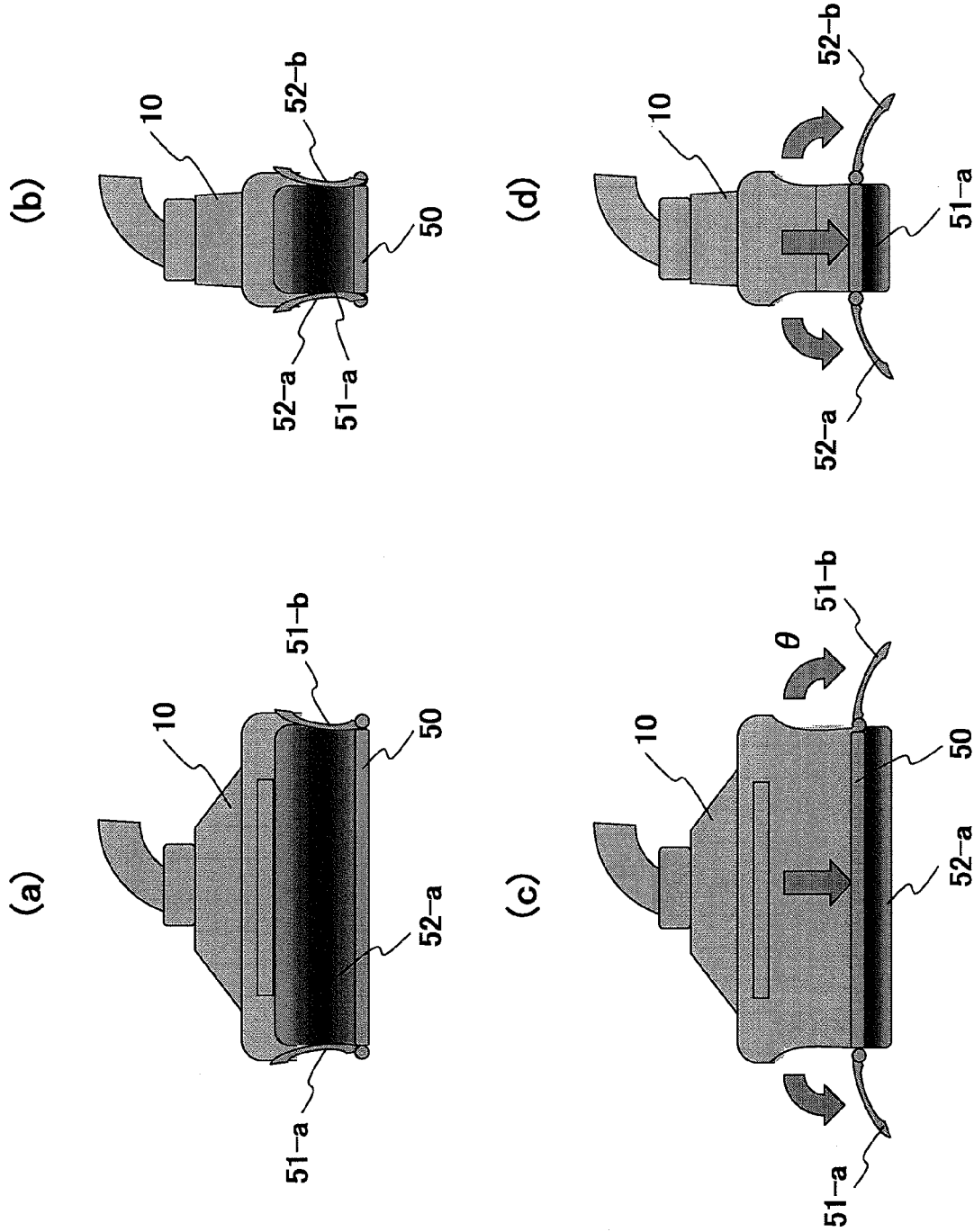
FIG. 7 is a diagram showing an eighth according to the present invention.

Next, an eight embodiment of the present invention will be described with reference to FIG. 7. FIG. 7(a) shows the pressing plate for pressing the subject 5 and the probe 10 when they are viewed in the major axis direction. FIG. 7(b) shows the pressing plate and the probe 10 when they are viewed in the minor axis direction. The difference from each of the above-described embodiments resides in that the side surfaces of the probe 10 are provided with a structure that the edge portion of the pressing plate (the second member) is divided into plural parts and these parts can be opened/closed. That is, both the side surfaces in the minor axis direction of the probe 10 are provided with retractable pressing plate edge portions 51-*a* and 51-*b* respectively, and both the side surfaces in the major axis direction of the probe 10 are provided with retractable pressing plate edge portions 52-*a* and 52-*b*. The pressing plate edge portions 51-*a* and 51-*b* have the same-level width as the width in the minor direction of the probe 10, and the pressing plate edge portions 52-*a* and 52-*b* have the same-level width as the width in the major axis direction of the probe 10. The contact surface of the press plate edge portion with the subject may be designed in a flat shape or in a curved shape, and FIG. 7 shows an example in which the contact surface concerned has a curved surface which is concaved to the subject 5 side. Furthermore, one end of each pressing plate edge portion is retractably connected to the side surface of the flat portion (first member) 50 through a hinge or the like. The flat portion 50 is formed so as to extend to the side surface in the neighborhood of the acoustic lens of the probe 10, that is, the ultrasonic wave transmission/reception face 11. The opening/closing of the edge portions of the pressing plate may be performed independently of one other or interlockingly with one another.

When the pressing plate is not being used, each edge portion of the pressing plate is kept folded toward the probe 10 side, and under this state the probe 10 is brought into contact with the subject 5 as in the case of the probe having no pressing plate. FIGS. 7(*c*) (*d*) shows the state that the pressing plate is being used. FIG. 7(*c*) shows the pressing plate and the probe 10 under the state that the pressing plate edge portions are unfolded when they are viewed in the major axis direction. FIG. 7(*d*) shows the pressing plate and the probe 10 under the state that the pressing plate edge portions are unfolded when they are viewed in the minor axis direction. The edge portions 51-*a*, 51-*b*, 52-*a*, 52-*b* of the pressing plate are tilted at an angle of $\theta$ from the side surface of the probe 10 to the subject 5 side, and form the whole of the pressing plate together with the flat portion 50. This angle $\theta$ is preferably variable in accordance with the curved surface shape of the body surface of the subject. For example, it can be implemented by a structure in which a proper angle is selected from preset angles of plural stages and fixed. Specifically, in the case of a linear probe 10 shown in FIG. 7, the angle $\theta$ is preferably set to 90 degrees or more because the tissue of the subject is pressed inwardly (that is, to the center portion side of the probe 10). In the case of the convex type probe shown in FIG. 5, the angle $\theta$ at which the pressing plate edge portion of the side surface of the probe in the minor axis direction is tilted is preferably set to be less than 90 degrees. Furthermore, it is preferable that the pressing plate edge portion of the side surface in the major axis direction of the convex type probe is divided to plural parts in the major axis direction, and these parts are tilted at 90 degrees or more from the side surface in the major axis direction of the probe and fixed.

As described above, according to the pressing plate structure of this embodiment, a work of mounting the pressing plate separately can be omitted. By unfolding the pressing plate edge portions in the course of the image pickup operation of tomograms, elastic images of the same site can be sequentially picked up. Conversely, by folding the pressing plate edge portions in the course of the image pickup operation of elastic images, tomograms of the same site can be sequentially picked up. Therefore, the image diagnosis can be efficiently performed.

(Ninth Embodiment)

Figure 8:
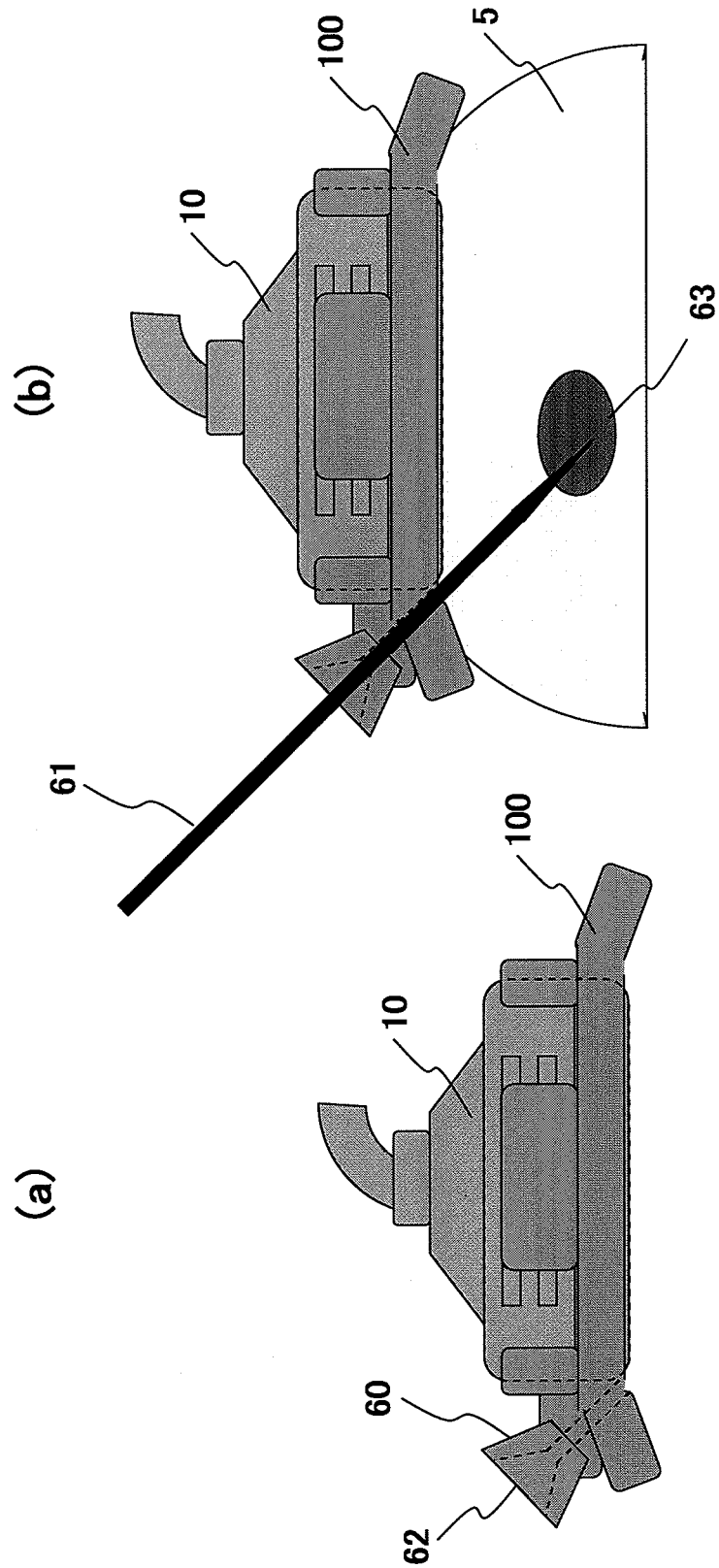
FIG. 8 is a diagram showing a ninth embodiment according to the present invention.

Next, a ninth embodiment of the present invention will be described with reference to FIG. 8. FIGS. 8(*a*) (*b*) show the pressing plate 100 for pressing the subject 5 and the probe 10 when they are viewed in the major axis direction. The difference from each of the above-described embodiments resides in that the pressing plate is provided with a puncture guide portion having a guide hole which penetrates through the pressing plate to guide a puncture needle. In FIG. 8, the same pressing plate 100 as shown in FIG. 2(*a*) is used. However, the pressing plate of this embodiment is not limited to the pressing plate 100, and the puncture guide portion may be provided to pressing plates having other shapes.

As shown in FIG. 8(*a*), the pressing plate 100 is equipped with a puncture guide portion 60 on the side surface side in the minor axis direction of the probe 10. A guide hole 62 for guiding a puncture needle 61 is provided to the center portion of the puncture guide portion 60 so as to penetrate through the pressing plate, and the puncture needle 61 is inserted into the subject 5 by inserting the puncture needle 61 through the guide hole 62. FIG. 8(*b*) shows an example in which the puncture needle 61 is inserted into the guide hole 62 of the puncture guide portion 60 and the puncture needle 61 is inserted till a puncture site 63 of the subject 5. FIG. 8 shows an example in which the puncture guide portion 60 is provided to one side surface in the minor axis direction of the probe 10. However, the puncture guide portion 60 may be provided to the opposite side surface side in the minor axis direction, or to one side surface side in the major axis direction, or plural puncture guide portions 60 may be provided to plural places.

The puncture guide portion 60 may be disposed on the pressing plate 100 while it has a mechanism for varying the guide angle of the puncture needle 61 in accordance with the position of the puncture site 63 (for example, plural guide holes which are different in angle are provided as disclosed in Patent Document 3). When the puncture site 63 is located at a deep portion, the puncture needle 61 is fixed in proximity to the side surface in the minor axis direction of the probe 10 so that the guide angle is small with respect to the side surface in the minor axis direction of the probe 10. Conversely, when the puncture site 63 is located at a shallow portion, the puncture needle 61 is fixed so as to be kept at a distance from the side surface in the minor axis direction of the probe 10 so that the guide angle is large with respect to the side surface in the minor axis direction of the probe 10.

The probe may be configured to be equipped with the pressing plate having the puncture guide portion of this embodiment in advance as in the case of the first embodiment.

As described above, according to the pressing plate structure of this embodiment, the puncture can be performed while the pressing plate does not obstruct, and also the puncture can be performed while properly guided. Therefore, the image diagnosis and the remedy and tissue diagnosis based on puncture can be efficiently performed.

Patent Document 3: JP-A-8-617

(Tenth Embodiment)

Figure 9:
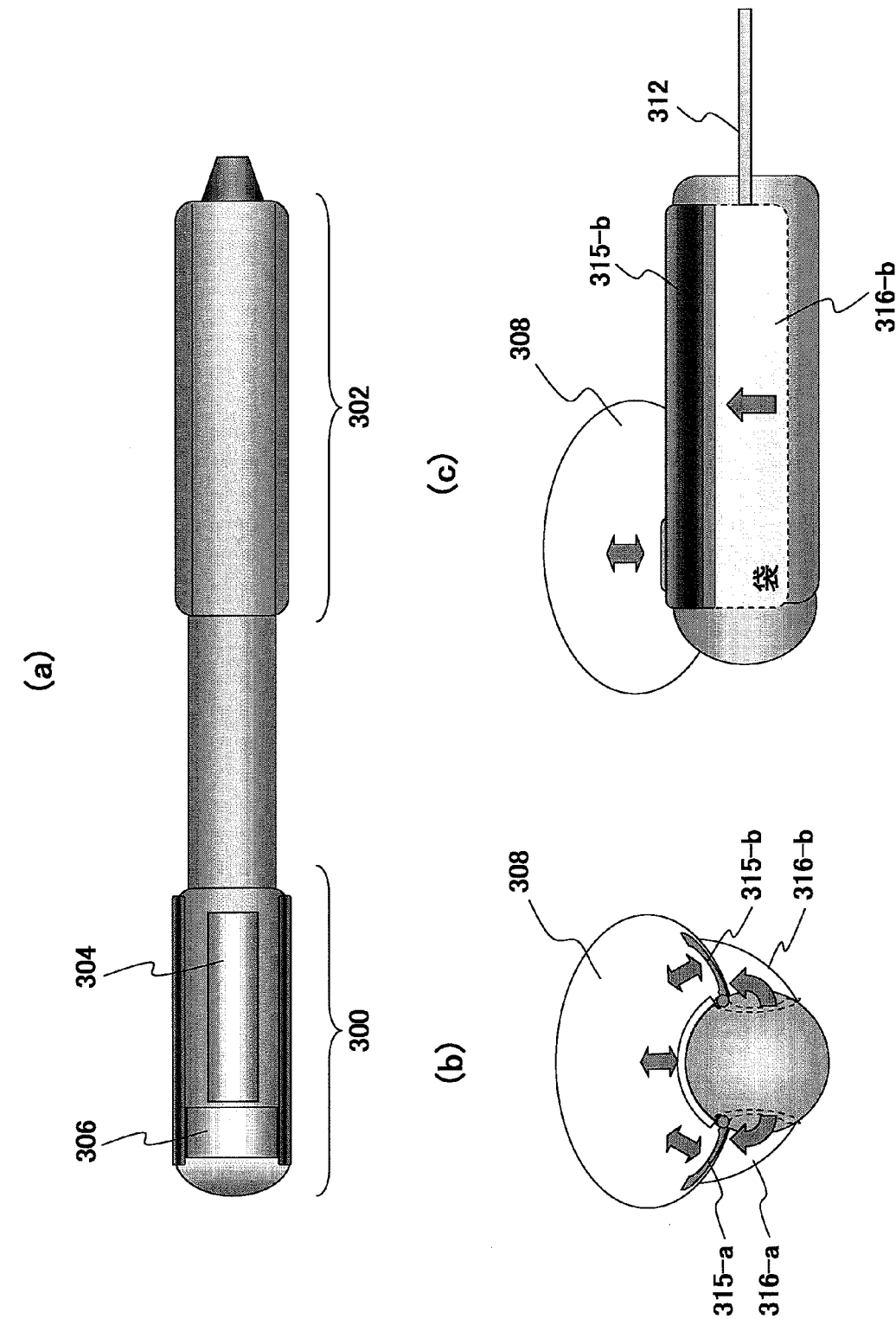
FIG. 9 is a diagram showing the ninth embodiment according to the present invention.

Next, a tenth embodiment of the present invention will be described with reference to FIG. 9. FIG. 9 shows the same transrectal ultrasonic probe as shown in FIG. 6. FIG. 9(*a*) shows the transrectal ultrasonic probe when it is viewed in the major axis direction thereof. FIG. 9(*b*) is a view taken from the tip of the body insertion portion 300 in the minor axis direction. FIG. 9(*c*) is a view taken in the major axis direction of the body insertion portion 300. In the transrectal ultrasonic probe shown in FIG. 9, the ultrasonic wave transmission/reception face 315 is brought into contact with the inner surface of the rectum of the subject 5, and the body insertion portion 300 has the ultrasonic wave transmission/reception face on which the biplane type ultrasonic transmission/reception portions 304 and 306 are disposed as in the case of the transrectal ultrasonic probe shown in FIG. 6.

The housing at the ultrasonic wave transmission/reception portion side of the body insertion portion 300 also functions as the first member of the pressing plate, and both the side surfaces of the body insertion portion 300 are provided with movable pressing plate edge portions (second members) 315-a and 315-b. One end of each pressing plate edge portion is movably connected to the side surface of the body insertion portion 300 through a hinge. The surfaces of the pressing plate edge portions 315a and 315-b at the body insertion portion side are joined to bag portions 316-a and 316-b, respectively. The bag portion 316 is joined to the pressing plate edge portion 315 and the body insertion portion 300 and disposed therebetween. By injecting liquid or gas into the bag portion 316, the pressing plate edge portions 315 are spread out and set to the state shown in FIGS. 9(b) (c). Furthermore, by exhausting liquid or gas from the bag portion 316, the pressing plate edge portions 315 are folded and retracted to the position indicated by a dashed line shown in FIGS. 9(b) (c). The bag portion 316 is connected to a pump (not shown) disposed at the outside of the subject through a tube 312, and the injection or exhaust of liquid or gas into or from the bag portion 316 is carried out by the pump.

Before the body insertion portion 300 is inserted into the rectum of the subject 5, each pressing plate edge portion 315 is folded, and the body insertion portion 300 is kept in a substantially cylindrical shape so as to be easily inserted. After the body insertion portion 300 is inserted into the rectum and the ultrasonic wave transmission/reception face comes into contact with the inner surface of the rectum, liquid or gas is injected into the bag portion 316 to spread out the pressing plate edge portions 315. The spread-out pressing plate edge portions 315 expands the contact area with the inner surface of the rectum, and thus the inner surface of the rectum can be effectively pressed. After the image pickup operation, the liquid or gas is exhausted from the bag portion 316, and thus the pressing plate edge portions 315 are folded and returned to the original positions. Under this state, the body insertion portion 300 is take out to the outside of the rectum.

It may be possible that the pressing plate end portions 315 are not provided, and only the bag portion 316 is provided and expanded to form a broad-range contact surface, thereby pressing the inner surface of the rectum.

As described above, according to the pressing plate structure of this embodiment, the transrectal ultrasonic probe is provided with the pressing plate edge portions, whereby the transrectal ultrasonic probe can be easily inserted and taken out and also the stress in the rectum can be efficiently performed. Accordingly, the image diagnosis of the rectum can be efficiently performed.

The embodiments of the present invention have been described. However, the pressing plate, the ultrasonic probe and the ultrasonic diagnosing device of the present invention are not limited to the contents disclosed in the description of the embodiments, and other embodiments can be adopted within the subject matter of the present invention.

For example, in the description of each embodiment, with respect to the pressing to the subject 5, an examiner may press the subject 5 while viewing elastic images displayed on the image display portion 24 and manually carrying out minute adjustment, or the probe 10 may be equipped with a pressing motor to automatically press the subject 5 by driving the motor as disclosed in Patent Document 2. When the pressing is carried out by driving the motor, the driving operation of the motor may be controlled in accordance with the type of the pressing plate.

Furthermore, when a pressing plate having a sharp slope at the edge portion thereof is used, the probe 10 is greatly moved up and down so that the elastic image of the region of the deep portion is efficiently displayed, and when a relatively small pressing plate is used, the probe 10 is finely vibrated.

Still furthermore, the mode in which the pressing plate is detachable from the probe 10 and the mode in which the probe and the pressing plate are formed integrally with each other are adopted in the description of the above-described embodiments. However, these modes may be reversed and applied.

In the description of some embodiments, a hole is formed at apart(for example, the center portion) of the pressing plate so that the acoustic lens of the probe 10, that is, the ultrasonic wave transmission/reception face 11 can be disposed in the pressing plate. However, it is unnecessary to provide a hole to the pressing plate insofar as the pressing plate is constructed by a member through which ultrasonic waves are transmitted.

The invention claimed is:

1. A pressing member that is detachable mounted to an ultrasonic probe to press against a subject for obtaining an elastic image of said subject, comprising:
a first member for transferring pressing force in a direction parallel to a pressing direction to the subject; and
a second member for transferring pressing force in a direction different from the pressing direction,
wherein:
the second member is formed so as to extend to the edge portion of the first member,
the direction different from the pressing direction is a direction facing the center portion side of the first member so that the pressing force is transferred in a direction intersecting with the pressing direction,
the first member has a first face vertical to the pressing direction, and the second member has a second face vertical to the direction different from the pressing direction,
at least one of the first face and the second face has a smooth varying concave shape at at least a part thereof, and
the first face and the second face are integral with each other to form a smoothly varying concave shape.

2. A pressing member that is detachably mounted to an ultrasonic probe to press against a subject for obtaining an elastic image of said subject, comprising:
a first member for transferring pressing force in a direction parallel to a pressing direction to the subject; and
a second member for transferring pressing force in a direction different from the pressing direction,
wherein:
the second member is formed so as to extend to the edge portion of the first member,
the direction different from pressing direction is a direction facing the center portion side of the first member so that the pressing force is transferred in a direction intersecting with the pressing direction,
the first member has a first face vertical to the pressing direction, and the second member has a second face vertical to the direction different from the pressing direction, and
the second member is formed along at least one of the minor axis direction and the major axis direction of the first member.

3. The pressing member according to claim 2, wherein the second member is formed so as to press in a direction along which a part of the subject pressed by the first member is prevented from being pushed out in the direction different from the pressing direction.

4. The pressing member according to claim 2, wherein at least one of the first face and the second face has a flat face at at least a part thereof.

5. The pressing member according to claim 2, wherein at least one of the first face and the second face is formed so as to have a smoothly varying convex shape at at least a part thereof.

6. The pressing member according to claim 2, wherein a face formed along the minor axis direction of the pressing member in the second face is formed obliquely to the first face so as to face the center portion side in the major axis direction of the pressing member, and a face formed along the major axis direction of the pressing member in the second face is formed obliquely to the first face so as to face the center portion side in the minor axis direction of the pressing member.

7. The pressing member according to claim 2, further comprising a guide portion having a guide hole that penetrates through the pressing member to guide a puncture needle.

8. The pressing member according claim 2, mounted on the ultrasonic probe, wherein the first face has a face parallel to an ultrasonic wave transmission/reception face of the ultrasonic probe, and the second face has a face that faces the center portion side of the ultrasonic wave transmission/reception face.

9. An ultrasonic probe having a pressing portion for pressing a subject for obtaining an elastic image of said subject, wherein the pressing portion has a first member for transferring pressing force to the subject in a direction parallel to the pressing direction, and a second member for transferring pressing force in a direction different from the pressing direction,
wherein:
the first member is formed so as to extend to the side surface of the ultrasonic probe, and the second member is formed so as to extend to the edge portion of the first member,
the first member has a first face parallel to an ultrasonic wave transmission/reception face of the ultrasonic probe, and the second member has a second face that is formed so as to face the center portion side of the ultrasonic wave transmission/reception face, and
the second member has a movable connecting portion and is connected to the edge portion of the first member so as to be foldable to the side surface side of the ultrasonic probe.

10. The ultrasonic probe according to claim 9, further comprising a body insertion portion adapted to be inserted into a body cavity of the subject, wherein the first member is formed integrally with a housing of the body insertion portion, and the second member is formed so as to be foldable to the side surface side in the minor axis direction of the body insertion portion.

11. The ultrasonic probe according to claim 10, further comprising a bag portion between the pressing portion and the side surface in the minor axis direction of the body insertion portion, wherein the pressing portion is spread out by injecting liquid or gas into the bag portion, and the pressing portion is folded by exhausting the liquid or the gas from the bag portion.

12. The ultrasonic probe according to claim 10, wherein the pressing portion is equipped with a guide portion having a guide hole that penetrates through the pressing portion to guide a puncture needle.

* * * * *